United States Patent
Legay et al.

(10) Patent No.: US 11,534,616 B2
(45) Date of Patent: Dec. 27, 2022

(54) SUBCUTANEOUS IMPLANTABLE CARDIAC DEFIBRILLATION SYSTEM

(71) Applicant: SORIN CRM SAS, Clamart (FR)

(72) Inventors: Thierry Legay, Fontenay les Briis (FR); Rafael Cordero Alvarez, Paris (FR); Delphine Feuerstein, Boulogne Billancourt (FR)

(73) Assignee: Sorin CRM SAS, Clamart (FR)

( * ) Notice: Subject to any disclaimer, the term of this patent is extended or adjusted under 35 U.S.C. 154(b) by 15 days.

(21) Appl. No.: 16/920,118

(22) Filed: Jul. 2, 2020

(65) Prior Publication Data

US 2021/0001137 A1 Jan. 7, 2021

(30) Foreign Application Priority Data

Jul. 5, 2019 (FR) ...................................... 1907532

(51) Int. Cl.
*A61N 1/00* (2006.01)
*A61N 1/39* (2006.01)
*A61N 1/375* (2006.01)

(52) U.S. Cl.
CPC ......... *A61N 1/3956* (2013.01); *A61N 1/3752* (2013.01); *A61N 1/3925* (2013.01)

(58) Field of Classification Search
CPC .. A61N 1/3956; A61N 1/3752; A61N 1/3925; A61N 1/39622; A61N 1/05; A61N 1/395; A61N 1/3968
See application file for complete search history.

(56) References Cited

U.S. PATENT DOCUMENTS

| | | | |
|---|---|---|---|
| 5,456,706 | A | 10/1995 | Pless et al. |
| 2014/0330325 | A1* | 11/2014 | Thompson-Nauman ................... A61N 1/39622 607/4 |

(Continued)

FOREIGN PATENT DOCUMENTS

| | | |
|---|---|---|
| DE | 19800697 A1 | 4/2009 |
| JP | 2006-518631 | 8/2006 |

(Continued)

OTHER PUBLICATIONS

European office action on EP Application No. 20183494.2 dated Nov. 11, 2020. 7 pages.

(Continued)

*Primary Examiner* — Scott M. Getzow
(74) *Attorney, Agent, or Firm* — Foley & Lardner LLP

(57) ABSTRACT

A subcutaneous cardiac defibrillation system implantable comprising a housing and a subcutaneous implantable lead comprising a proximal end connected to the housing and a distal free end. The subcutaneous implantable lead comprises at least one defibrillation electrode and at least three detection electrodes. The first detection electrode and the second detection electrode form a first dipole, and the third detection electrode and the first detection electrode, or the third detection electrode and the second detection electrode, or the housing and one of said detection electrodes, form a second dipole. The defibrillation electrode is positioned between the second detection electrode and the third detection electrode, the first dipole is positioned between the housing and the defibrillation electrode, the third electrode is positioned between the free distal end of the lead and the defibrillation electrode, and the length of the first dipole is shorter than the length of the second dipole.

10 Claims, 2 Drawing Sheets

(56) References Cited

U.S. PATENT DOCUMENTS

| | | | |
|---|---|---|---|
| 2015/0112414 A1* | 4/2015 | Conger | A61N 1/05 607/116 |
| 2015/0306410 A1 | 10/2015 | Marshall et al. | |
| 2017/0312494 A1 | 11/2017 | Seifert et al. | |
| 2019/0054290 A1* | 2/2019 | De Kock | A61N 1/0504 |
| 2019/0298991 A1 | 10/2019 | Bomzin et al. | |

FOREIGN PATENT DOCUMENTS

| WO | WO-92/17240 A1 | 10/1992 |
|---|---|---|
| WO | WO-2017/192870 A1 | 11/2017 |

OTHER PUBLICATIONS

Foreign Search Report for FR Application No. 1907532 dated Feb. 28, 2020. 8 pages.
Office Action issued in Japanese Application No. 2020-115478 dated Aug. 13, 2021. 10 pages.

* cited by examiner

SUBCUTANEOUS IMPLANTABLE CARDIAC DEFIBRILLATION SYSTEM

CROSS-REFERENCE TO RELATED PATENT APPLICATIONS

This application claims the benefit of and priority to French Application No. 1907532, filed Jul. 5, 2019, which is incorporated herein by reference in its entirety.

BACKGROUND

The present invention relates to a subcutaneous implantable cardiac defibrillation system.

Conventional implantable automatic defibrillators, i.e. of transvenous type, also abbreviated ICD for "Implantable Cardioverter-Defibrillator", comprise a defibrillation pulse generator and a microprocessor control unit housed in a metal case usually implanted in the chest pocket. This box is connected to one or more leads which are introduced into the subclavian vein where they finally reach the heart. Inside the heart, the distal ends of the leads are attached to the inner walls of the heart chambers, where they can record electrograms (EGMs) reflecting the electrophysiological functioning of the heart. Based on these, defibrillation therapy (defibrillation shock) is administered (or discontinued) to end a life-threatening ventricular tachyarrhythmia, such as ventricular tachycardia and ventricular fibrillation.

The weakest components of these transvenous implantable automatic defibrillators (as well as pacemakers and similar devices) are the intracardiac leads. One of the most common causes of pacemaker dysfunction is lead fracture. Extraction of an implanted ICD lead (or of a pacemaker) is a procedure with high morbidity and high mortality, and is therefore generally only performed in cases of severe systemic infection that cannot be treated with antibiotics. In most cases, the fractured leads will be disconnected from the device and left in the heart. A new lead is then implanted next to the old one and connected to the implantable automatic defibrillator. However, this solution is only possible if there is still enough space in the vein, since the presence of more leads can lead to venous occlusion. Therefore, the use of intracardiac leads is not ideally suited for young patients, who may need a multitude of leads over their lifetime.

One solution to the problems associated with intracardiac leads, listed above, is to replace them with subcutaneous leads. Thus, in the absence of contact with the heart or blood, the risk of systemic infection is eliminated and the veins are no longer obstructed. In addition, unlike intracardiac leads, the extraction of subcutaneous leads is less traumatic and does not involve any risk of mortality, since the subcutaneous leads is not in contact with the heart. As a result, the leads can be safely removed in the event of a fracture and replaced with new subcutaneous leads, without risk to the patient.

The main challenges of subcutaneous implantable devices are related to reducing the signal-to-noise ratio of signals recorded subcutaneously and increasing the energy required for successful defibrillation. Subcutaneous implantable devices record subcutaneous electrocardiograms (ECG—FIG. 1 illustrates a typical plot representing a normal ECG)—rather than EGM—which capture spatially averaged far field electrophysiological activity. P and T waves are more significant in subcutaneous ECGs than in intracardiac EGMs, which makes it more difficult to detect R waves and therefore calculate RR intervals using tachyarrhythmia detection algorithms. An incorrect interpretation of the signals collected could lead, for example in an implantable automatic defibrillator, to an inappropriate shock, which can be traumatic or even harmful for the patient. Non-cardiac noise sources, such as myopotentials, can also alter subcutaneous signals and interfere with detection algorithms, which disrupts processing. In addition, subcutaneous signals tend to be more sensitive to changes in posture than intracardiac signals.

SUMMARY

In order to overcome the above-mentioned limitations, the object of the present invention is to improve the detection, in particular in terms of sensitivity and discrimination, of the electrophysiological signals recorded by a subcutaneous implantable cardiac defibrillation system.

The object of the present invention is achieved by a subcutaneous implantable cardiac defibrillation system comprising a housing; and a subcutaneous implantable lead comprising two ends, a proximal end being connected to the housing and a distal end being a free end; the subcutaneous implantable lead comprising at least one defibrillation electrode and at least three detection electrodes; the first detection electrode and the second detection electrode forming a first dipole; the third detection electrode and the first detection electrode, or the third detection electrode and the second detection electrode, or the housing and one of said detection electrodes, forming a second dipole; the defibrillation electrode being positioned between the second detection electrode and the third detection electrode; the first dipole being positioned between the housing and the defibrillation electrode; the third electrode being positioned between the free distal end of the lead and the defibrillation electrode; and the length of the first dipole being shorter than the length of the second dipole.

The first dipole, by the specificity of its positioning on the lead and its size compared to the second dipole, makes it possible to selectively detect electrophysiological signals improving the detection of the R wave and minimizing that of the P and T cardiac waves. Such an arrangement of the first dipole thus makes it possible to improve the measurement of the RR interval. In addition, this specific configuration of the dipoles of the subcutaneous implantable cardiac defibrillation system also makes it possible to reduce the noises and artefacts, for example generated by the muscle mass of the patient, to which the first dipole is less susceptible being shorter than the second dipole, and therefore to further improve the quality of the detection of the electrophysiological signal, in particular by reducing the risks of over-detection.

The present invention, relating to a subcutaneous implantable cardiac defibrillation system, can be further improved by means of the following embodiments.

According to one embodiment of the invention, the subcutaneous implantable cardiac defibrillation system can further comprise a controller configured for the detection of electrophysiological signals concurrently recorded via the first dipole and the second dipole of the subcutaneous implantable lead; the controller can be configured for the detection of the R wave of an electrophysiological signal via the first dipole.

The first dipole, being shorter than the second dipole, is less exposed to the risk of over-detection. Indeed, the distance covered between the electrodes of the first dipole is reduced compared to that of the second dipole, which reduces the risk of signal alteration by an external source.

There is, for example, less muscle mass between the electrodes of the first dipole, which risks introducing myopotentials. Detection of the R wave via the first dipole thus improves the quality of the detection of the R wave compared to known subcutaneous implantable cardiac defibrillation systems. Thus, the measurement of the R-R interval can be further improved.

According to one embodiment of the invention, the length of the first dipole, i.e. the distance between the first detection electrode and the second detection electrode, can be between 5 and 50 millimeters, in particular between 10 and 20 millimeters; and the length of the second dipole is the distance between the third detection electrode and the first detection electrode, or, the third detection electrode and the second detection electrode, or, the housing and one of said detection electrodes, can be between 50 and 400 millimeters.

It turns out that an improvement in the quality of the signals detected via the first dipole and the second dipole is exhibited at these specific lengths.

According to one embodiment of the invention, the subcutaneous implantable lead can comprise at least one fixing means for fixing the lead to the tissues of a patient.

The positioning of the subcutaneous implantable lead is then ensured by the means for fixing, thus avoiding involuntary displacement of the lead during a movement of the patient for example. Such involuntary displacement could modify the position of the first dipole and the second dipole relative to the patient's body, and affect the quality of the electrophysiological signals detected via these dipoles.

According to one embodiment of the invention, the at least one means for fixing the subcutaneous implantable lead can be positioned between the second detection electrode and the defibrillation electrode.

This particular positioning of the fixing means makes it possible in particular to bend the lead at the level of the fixing means so as to form an angle, in particular essentially a right angle, between the portions of the lead which are on either side of this means of fixation.

According to one embodiment of the invention, the at least one means for fixing the subcutaneous implantable lead can be positioned between 60 and 300 millimeters from the proximal end; and the at least one means for fixing the subcutaneous implantable lead can be positioned between 50 and 400 millimeters from the distal end.

An improvement in the quality of the signals detected via the first dipole and the second dipole is exhibited at these specific dimensions. Indeed, these specific dimensions allow both to define the positioning of the first dipole and the second dipole relative to each other, but also relative to the muscle mass of a patient when the system is implanted—the housing of such a system being usually implanted in the same place in each patient, that is to say on the left side of the patient's chest according to known medical practices.

According to one embodiment of the invention, the at least one means for fixing the subcutaneous implantable lead can be a groove on the circumference of the subcutaneous implantable lead, the width of the groove being dimensioned to accommodate a ligature wire therein.

The attachment means is thus adapted so that a practitioner can perform a ligature of the subcutaneous lead to the muscle mass of the patient, and thus ensure the maintenance and positioning of the subcutaneous lead and its dipoles.

According to an embodiment of the invention, the distance between the housing and the first detection electrode can be between 40 and 300 millimeters.

An improvement in the quality of the signals detected via the first dipole is exhibited at this specific dimension of the first electrode relative to the housing, in particular because it is adapted to be able to position the first dipole of the lead above the cardiac notch of the left lung.

According to one embodiment of the invention, the subcutaneous implantable defibrillator can further comprise an accelerometer or/and a gyroscope configured to detect the position of the patient.

By allowing the detection of the patient's position, the interpretation of the detected electrophysiological signals is further refined, and therefore improved.

According to an embodiment of the invention, the second dipole can be formed by the third detection electrode and the second detection electrode.

The second dipole formed by the third detection electrode and the second detection electrode has a geometry more suitable for improving the detection of electrophysiological signals, in particular when the lead is bent essentially perpendicularly to the level of the fixing means. Indeed, such a perpendicular arrangement between the second detection electrode and the third detection electrode makes it possible to improve the quality of the signal detected by the second dipole.

BRIEF DESCRIPTION OF THE DRAWINGS

The invention and its advantages will be explained in more detail below by means of preferred embodiments and based in particular on the following accompanying figures, wherein.

DETAILED DESCRIPTION

The invention will now be described in more detail using advantageous embodiments in an exemplary method and with reference to FIGS. 2 and 3. The embodiments described are simply possible configurations and it should be borne in mind that the individual characteristics as described above can be provided independently of each other or can be omitted altogether when practicing the present invention.

Figure 1:
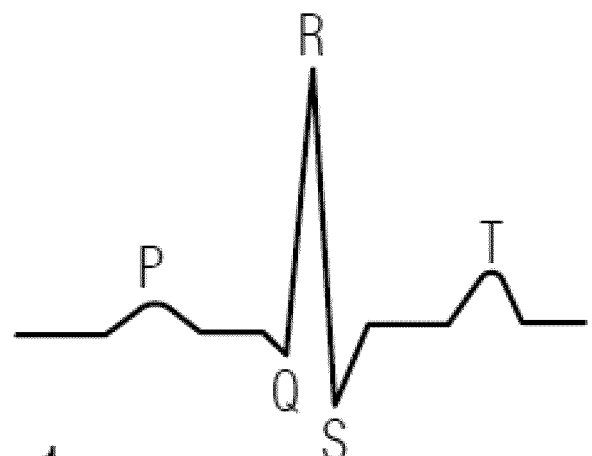
FIG. 1 represents a schematic plot of a normal electrocardiogram.
Figure 2:
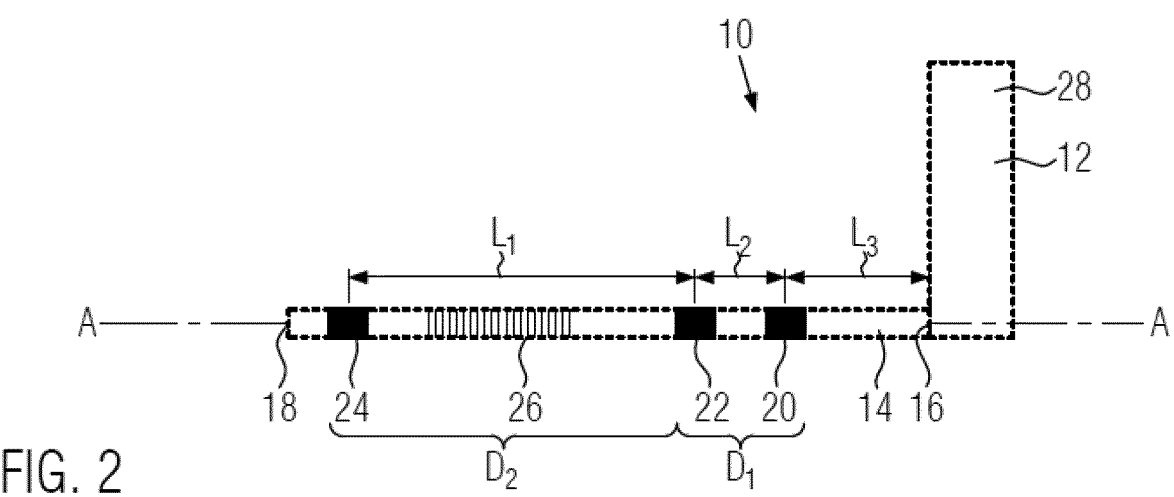
FIG. 2 represents a schematic view of a subcutaneous implantable cardiac defibrillation system according to the present invention.

FIG. 2 illustrates a cardiac defibrillation system implantable under the skin 10. FIG. 3 illustrates said system 10 in an implanted state.

The subcutaneous implantable cardiac defibrillation system 10 comprises a pulse generator housing 12, to which a subcutaneous implantable lead 14 is connected. The subcutaneous implantable cardiac defibrillation system 10 is capable of delivering a defibrillation shock.

The subcutaneous implantable lead 14 is at least partially flexible and comprises two ends 16, 18: a proximal end 16 which is connected to the housing 12 and a free distal end 18.

Figure 3:
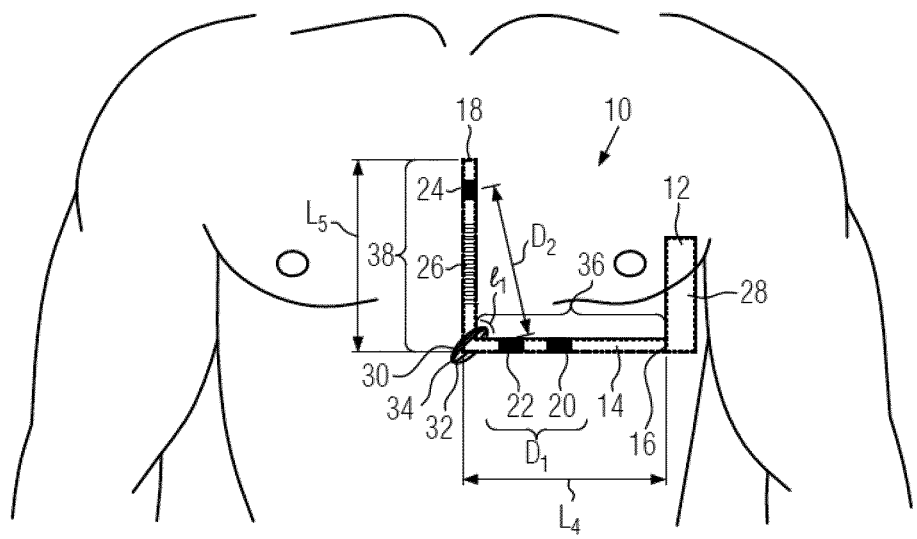
FIG. 3 represents a schematic and transparent view of the subcutaneous implantable cardiac defibrillation system according to the present invention.

In the embodiment illustrated in FIGS. 2 and 3, the subcutaneous implantable lead 14 comprises three detection electrodes 20, 22, 24 and a defibrillation electrode 26. In a variant, the subcutaneous implantable lead 14 could comprise more than three detection electrodes.

The subcutaneous implantable lead 14 also comprises conductive wires (which are not visible in FIGS. 2 and 3) making it possible to electrically connect the electrodes 20, 22, 24 of the lead 14 to electrical contacts (not visible in FIGS. 2 and 3) at the housing 12—known per se in the current state of the art.

In an advantageous embodiment, at least one of the detection electrodes 20, 22 is formed of a monofilament (not shown) wound around the implantable subcutaneous lead 14. Thus, in this embodiment, at least one of the detection electrodes 20, 22 is a flexible electrode unlike known conventional leads which are provided with rigid detection rings. The detection electrodes 20, 22, 24 may be partially coated with an undercoat of silicone or polyurethane.

The detection electrodes 20, 22, 24 of the implantable subcutaneous lead 14 allow the detection of electrophysiological signals used to deduce the cardiac activity of a patient.

The detection of electrophysiological activity by the subcutaneous route is however impaired by numerous artefacts such as noises of muscular origin or interference with the external environment. In addition, the lead 14 being of the subcutaneous type, the detection electrodes 20, 22, 24 are not in direct contact with the myocardium. The quality of the detection of electrophysiological signals for an implantable subcutaneous defibrillator thus largely depends on the positioning of the detection electrodes 20, 22, 24.

In order to improve the detection of the R wave and to minimize that of the P and T cardiac waves, and to reduce the risk of over-detection or/and false detections, in particular to facilitate the measurement of the RR interval, the system of subcutaneous implantable cardiac defibrillation 10 comprises a specific positioning of the detection electrodes 20, 22, 24. Specifically, as illustrated in FIGS. 2 and 3, a first detection electrode 20 and a second detection electrode 22 are positioned between the housing 12 and the defibrillation electrode 26; while a third detection electrode 24 is placed between the distal end 18 of the lead 14 and the defibrillation electrode 26. The defibrillation electrode 26 is thus positioned between the second detection electrode 22 and the third detection electrode 24. Thus, in a direction extending from the proximal end 16 of the lead 14 to the distal end 18 of the lead 14, the lead comprises in this order: the first detection electrode 20, the second detection electrode 22, the defibrillation electrode 26 and then the third detection electrode 24.

The specific positioning of the detection electrodes 20, 22, 24 will be described in terms of length with reference to FIG. 2 only, representing the lead 14 in a non-implanted, non-curved state and aligned along an axis A.

The first detection electrode 20 and the second detection electrode 22 form a first dipole D1 of length L1.

According to the embodiment illustrated in FIG. 2, the second detection electrode 22 and the third detection electrode 24 form a second dipole D2 of length L2. In a variant, the second dipole D2 can be formed by the third detection electrode 24 and the first detection electrode 20. In another variant, the second dipole D2 can be formed by the housing 12 and one of the three detection electrodes 20, 22, 24.

The length L1 of the first dipole D1 is shorter than the length L2 of the second dipole D2. In particular, the length L1 is between 5 to 50 millimeters, more particularly between 10 and 20 millimeters, while the length L2 is between 50 and 400 millimeters. In addition, the distance L3 between the first detection electrode 20 and the housing 12 is between 40 and 300 millimeters.

The subcutaneous implantable cardiac defibrillation system 10 further comprises a controller 28 housed in the housing 12. The controller 28 of the system 10 is configured to detect electrical signals recorded simultaneously via the first dipole D1 and the second dipole D2 of the implantable lead under-cutaneous 14. The controller 28 is configured to detect the R wave of an electrophysiological signal at the level of the first dipole D1.

In another embodiment, the detection of the R wave via the first dipole could be combined with the detection of electrophysiological signals on a plurality of "second dipoles", i.e. on a plurality of dipoles which are longer than the first dipole, for example: a dipole formed by the second detection electrode 22 and the third detection electrode 24, a dipole formed by the first detection electrode 20 and the third detection electrode 24 and a dipole formed between the housing 12 and the third detection electrode 24. In a variant, the housing 12 can serve as an electrode for forming a second dipole with one of the detection electrodes 20, 22, 24.

As the first D1 dipole is shorter than the second D2 dipole, the first D1 dipole is less exposed to the risk of over-detection, in particular as it is less subject to recording noises of muscular origin. In addition, the first dipole D1 is positioned during the subcutaneous implantation of the system 10 near and above the left lung cardiac notch and the ventricles. This particular position of the first dipole D1 makes it possible to detect an electrophysiological signal with an R wave which is more distinctive compared to the P and T waves; the P and T waves detected at this location being minimized with respect to the R wave. This advantageous technical effect improving the detection of the R wave via the signals collected from the first dipole D1 is illustrated in FIG. 4.

Figure 4:
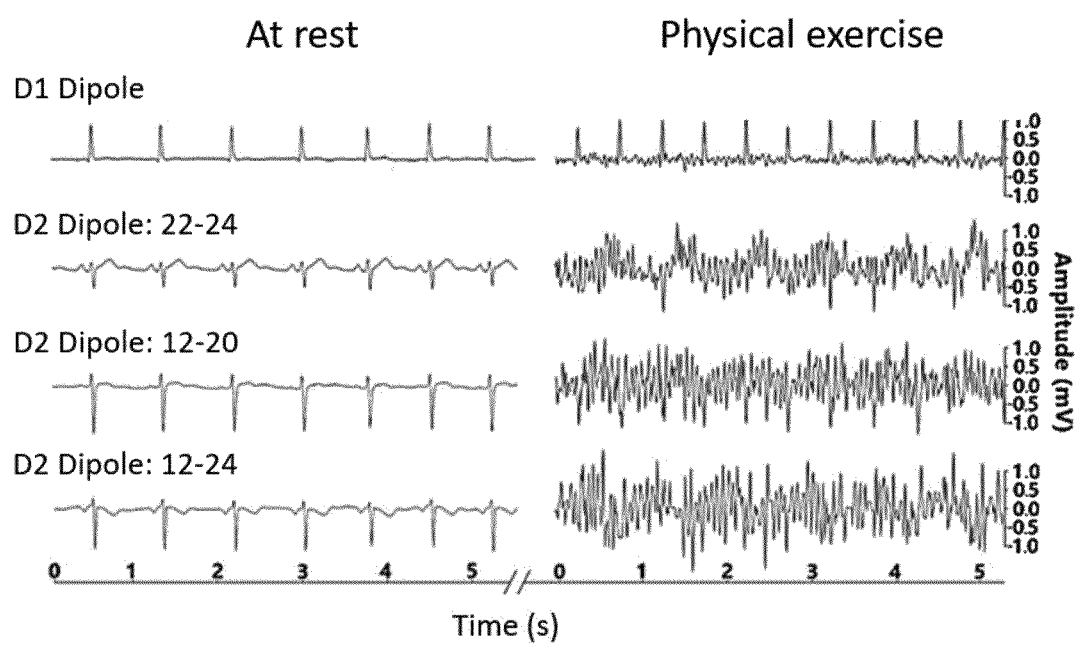
FIG. 4 represents electrophysiological signals collected by means of the subcutaneous implantable cardiac defibrillation system according to the present invention.

FIG. 4 represents several electrophysiological signals from a patient collected in a state known as "at rest" and during physical exercise, via the dipole D1 and three different configurations of dipole D2. According to a first configuration, the dipole D2 is formed by the second detection electrode 22 and the third detection electrode 24 (see "Dipole D2: 22-24 in FIG. 4). According to a second configuration, the dipole D2 is formed by the housing 12 and the first detection electrode 20 (see "Dipole D2: 12-20 in FIG. 4). According to a third configuration, the dipole D2 is formed by the housing 12 and the third detection electrode 24 (see "Dipole D2: 12-24 in FIG. 4).

The signals collected in the rest state demonstrate the method by which the dipole D1 has high R/T and R/P ratios, i.e. optimal, compared to the dipoles D2. The risk of over-detection of the T wave therefore turns out to be lower on the dipole D1. In addition, the signals collected during exercise show how myopotentials can affect the signals. However, the signals collected via the dipole D1 remain much less affected than those of the dipoles D2. Therefore, it is easier to detect the R wave on the dipole D1. The reason, already mentioned above, comes in particular from the fact that the first dipole D1 being shorter than the second dipole D2, the dipole D1 is less subject to recording noises of muscular origin, likely to alter the signals.

In order to allow the first dipole D1 and the second dipole D2 to be positioned relative to the patient's tissues, as illustrated in FIG. 3, so as to optimize the quality of the detected electrophysiological signal, the implantable subcutaneous lead comprises a fixing means 30.

The fixing means 30 is positioned between the second detection electrode 22 and the defibrillation electrode 26. The fixing means 30 of the implantable subcutaneous lead 14 is positioned at a distance L4 between 60 and 300 millimeters from the proximal end 16 of the lead 14 and at a distance L5 between 50 to 400 millimeters from the distal end 18 of the lead 14. Its specific dimensions L4 and L5 make it possible both to define the positioning of the first dipole D1 and of the second dipole D2 relative to each other, but also relative to the patient's muscle mass when the system 10 is implanted; the housing 12 is usually implanted in the same place in each patient, that is to say on the left side of the patient's chest according to known medical practices and as shown in FIG. 3.

The fixing means 30 also makes it possible to avoid an involuntary displacement of the implantable subcutaneous lead 14, for example generated by a movement of the patient. The fixing means 30 thus facilitates the maintenance of the adequate positions of the first dipole D1 and of the second dipole D2 relative to one another but also relative to the patient's body.

According to a non-limiting embodiment and illustrated in FIG. 2, the fixing means 30 comprises a groove 32 on the circumference of the implantable subcutaneous lead 14, the width 11 of the groove 32 being dimensioned to accommodate a wire therein a ligature wire 34. A practitioner can thus attach the implantable subcutaneous lead 14 to the tissues, for example the muscular tissues, of a patient by performing a subcutaneous ligature at the fixing means 30.

The positioning of the fixing means 30 on the implantable subcutaneous lead 14 also makes it possible to define the position of the change in curve of the implantable subcutaneous lead 14. In fact, when it is implanted subcutaneously, the implantable subcutaneous lead 14 is curved at the level of the fixing means 30 (see FIG. 3), so that a first portion 36 of the lead 14 between the proximal end 16 and the fixing means 30 is essentially perpendicular to a second portion 38 of the lead 14 between the distal end 18 and the fixing means 30. Thus, the first dipole D1 and the second dipole D2 are preferably arranged so as not to be aligned with one another. It turns out that this essentially perpendicular arrangement between the first portion 36 of the lead and the second portion 38 of the lead 14, produced at the level of the fixing means 30, makes it possible to further improve the quality of the detected signals, in particular because the perpendicularity of the portions 36, 38 of the implanted lead 14 makes it possible to detect signals in an almost orthogonal coordinate system. The fact that the signals detected via the first dipole and via the second dipole are collected in an almost orthogonal method makes it possible to provide two different perspectives of the electrophysiological signals, from which more information can be extracted and cross-checked with each other; only from one perspective. This information can be used to identify a patient's heart rate.

In another embodiment, the subcutaneous implantable cardiac defibrillation system 10 may further comprise an accelerometer or/and a gyroscope configured to detect the position of the patient. Therefore, by allowing the detection of the patient's position, the interpretation of the detected electrophysiological signals can be further refined, and therefore improved.

In another embodiment, the implantable subcutaneous lead 14 may further comprise an insulating means displaceable on the first portion 36 of the lead 14 so as to at least partially cover the first dipole D1—thus making it possible to offset the position of the dipole D1 on the first portion 36 of the lead 14.

Thus, the specific dimensions L1, L2 L3, L4 and L5 characterizing the subcutaneous implantable cardiac defibrillation system 10, the particular selection of the dipoles and the detection of the R waves recorded via the first dipole make it possible to improve the quality of the detection of the R wave of system 10 compared to known implantable subcutaneous cardiac defibrillation systems.

In another embodiment, the detection of the R wave via the first dipole could be combined with the detection of electrophysiological signals on a plurality of "second dipoles", i.e. on a plurality of dipoles which are longer than the first dipole, for example: a dipole formed by the second detection electrode 22 and the third detection electrode 24, a dipole formed by the first detection electrode 20 and the third detection electrode 24 and a dipole formed between the housing 12 and one of the detection electrodes 20, 22, 24.

The embodiments described are simply possible configurations and it should be borne in mind that the individual characteristics of the various embodiments can be combined with one another or provided independently of one another.

The invention claimed is:

1. A subcutaneous implantable cardiac defibrillation system comprising:
   a housing; and
   a subcutaneous implantable lead comprising two ends, including a proximal end being connected to the housing and a distal end being a free end;
   the subcutaneous implantable lead comprising at least one defibrillation electrode and at least three detection electrodes including a first detection electrode, a second detection electrode, and a third detection electrode;
   the first detection electrode and the second detection electrode forming a first dipole;
   the third detection electrode and the first detection electrode, or, the third detection electrode and the second detection electrode, or, the housing and one of said detection electrodes, forming a second dipole;
   the defibrillation electrode being positioned between the second detection electrode and the third detection electrode;
   the first dipole being positioned between the housing and the defibrillation electrode;
   the third electrode being positioned between the free distal end of the lead and the defibrillation electrode; and
   the length of the first dipole being shorter than the length of the second dipole.

2. The subcutaneous implantable cardiac defibrillation system of claim 1, further comprising a controller configured for the detection of electrical signals concurrently recorded via the first dipole and the second dipole of the subcutaneous implantable lead;
   the controller being configured for the detection of an R wave of the electrical signal via the first dipole.

3. The subcutaneous implantable cardiac defibrillation system of claim 1, wherein the length of the first dipole, that is the distance between the first detection electrode and the second detection electrode, is between 5 and 50 millimeters, in particular between 10 and 20 millimeters; and
   the length of the second dipole, that is the distance between the third detection electrode and the first detection electrode, or, the third detection electrode and the second electrode detection, or, the housing and one of said detection electrodes, is between 50 and 400 millimeters.

4. The subcutaneous implantable cardiac defibrillation system of claim 1, wherein the subcutaneous implantable lead comprises at least one fixing means for fixing the subcutaneous implantable lead to the tissues of a patient.

5. The subcutaneous implantable cardiac defibrillation system of claim 4, further comprising an accelerometer or/and a gyroscope configured to detect the position of the patient.

6. The subcutaneous implantable cardiac defibrillation system of claim 4, wherein the at least one fixing means of the subcutaneous implantable lead is positioned between the second detection electrode and the defibrillation electrode.

7. The subcutaneous implantable cardiac defibrillation system of claim 5, wherein the at least one fixing means of the subcutaneous implantable lead is positioned between 60 and 300 millimeters from the proximal end; and
   the at least one fixing means of the subcutaneous implantable lead is positioned between 50 and 400 millimeters from the distal end.

8. The subcutaneous implantable cardiac defibrillation system of claim 5, wherein the at least one fixing means of the subcutaneous implantable lead is a groove on the circumference of the subcutaneous implantable lead, the width of the groove being dimensioned to accommodate a ligature wire therein.

9. The subcutaneous implantable cardiac defibrillation system of claim 1, wherein the distance between the housing and the first detection electrode is between 40 and 300 millimeters.

10. The subcutaneous implantable cardiac defibrillation system of claim 1, wherein the second dipole is formed by the third detection electrode and the second detection electrode.

\* \* \* \* \*